United States Patent [19]

Ruffo

[11] Patent Number: 4,675,013
[45] Date of Patent: Jun. 23, 1987

[54] NAPKIN CONSTRUCTION WITH LAMINATE WRAPPER

[75] Inventor: Angelo P. Ruffo, Mount Royal, Canada

[73] Assignee: Johnson & Johnson, New Brunswick, N.J.

[21] Appl. No.: 654,066

[22] Filed: Sep. 25, 1984

[51] Int. Cl.[4] .............................................. A61F 13/16
[52] U.S. Cl. .................................... 604/366; 604/381; 604/385.1
[58] Field of Search ............... 604/381, 385, 387, 382, 604/359, 366, 370, 374, 375, 372, 383

[56] References Cited

U.S. PATENT DOCUMENTS

| | | | |
|---|---|---|---|
| 2,843,125 | 6/1958 | Bletzinger et al. | 604/382 |
| 3,230,955 | 1/1966 | Yoa et al. | 604/366 |
| 3,559,649 | 2/1971 | Grad | 604/382 |
| 4,389,211 | 6/1983 | Lenaghan | 604/383 |

Primary Examiner—John D. Yasko
Attorney, Agent, or Firm—Jason Lipow

[57] ABSTRACT

A sanitary napkin is provided which obviates the problem of stain propagating across the body facing side of the napkin while still facilitates manufacturing processes. Specifically, the napkin comprises a pad having a wrapper which overlies the garment facing side of the pad, the longitudinal sides of the pad, and peripheral portions of the body facing surface of the pad. The wrapper comprises a body fluid impervious sheet laminated to a fibrous sheet with the fibrous sheet being wider than the impervious sheet. The fibrous sheet has a width sufficient to overlie the garment facing surface, the longitudinal sides and the longitudinal peripheral portions of the body facing side of said pad, but is insufficient in width to overlie the central major portion of the body facing surface of the pad.

13 Claims, 7 Drawing Figures

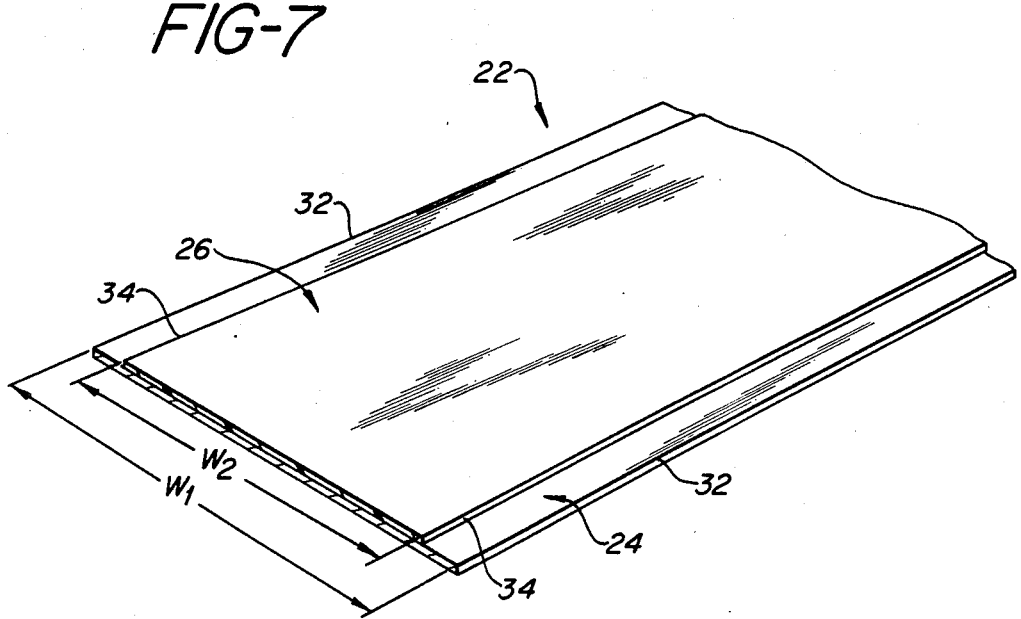

NAPKIN CONSTRUCTION WITH LAMINATE WRAPPER

BACKGROUND OF THE INVENTION

This invention relates to a sanitary napkin and, in particular, to one of a construction which incorporates a body fluid impervious layer that, for ease of manufacture, is laminated to a fibrous layer.

Sanitary napkins generally comprise a pad or core formed from one or more layers of hydrophilic material such as wood pulp, rayon, cotton, or some of the synthetic hydrophilic materials such as hydrophilic foams. The pad is generally rectangular in shape with one of its major surfaces designed to be worn against the body and the opposite major surface to be worn against the inner crotch portion of the user's undergarment. In order to protect such undergarment from stain and wetting, the garment facing surface and at least part of the longitudinal sides between major surfaces are covered by a body fluid impervious sheet. Such sheet generally comprises a thin film of a polyolefin with polyethylene being the material of choice in that polyethylene is highly suitable for this purpose, readily available and relatively inexpensive. The pad and its body fluid impervious sheet are generally overwrapped with an outer cover.

Recently, new products have been directed toward providing outer covers for such products which covers do not readily give a stained appearance after use. It has been discovered that such covers, comprised of hydrophobic materials such as hydrophobic fibrous fabrics or apertured films, will allow body fluid to pass readily into the absorbent pad but will not promote wicking of such fluid laterally along the surface of the cover and hence will limit the stained appearance of the cover to an essentially small fluid deposition area.

Unfortunately, it has been discovered that, in certain napkin constructions, the desirable attributes of non-staining are frustrated, notwithstanding the use of these newer cover materials. Specifically, certain napkin constructions have been employed wherein the body fluid impervious layer is laminated to a fibrous layer, e.g., tissue. This laminate structure has been employed primarily to facilitate the handling of the body fluid impervious material which generally has been in the form of a thin film which is slippery, flimsy, and subject to electrostatic charge and hence difficult to position properly about a pad during high speed manufacture. Further, the practice has been to manufacture such products by first wrapping a long snake or sliver of absorbent material with a continuous supply of impervious material and then subdividing or cutting such wrapped sliver into individual pads. Absent any processing aid, it has been essentially impossible to cut a wrapped sliver without displacing the impervious material.

Accordingly, one solution to this processing problem has been suggested in Canadian Patent Number 805,351 issued for "Napkin Construction" to Angelo P. Ruffo, et al. on Feb. 4, 1969. In accordance with the teachings of this Canadian patent, the impervious layer is laminated to a tissue layer which is substantially wider than the impervious layer and hence the longitudinal edges of the tissue layer extend beyond those of the impervious layer. This laminate is then wrapped about the pad so that the impervious layer extends to and covers the garment facing surface of the pad and a portion of the longitudinal sides of the pad. The wider tissue extends beyond the edges of the impervious layer and overlies the entire body facing surface of the pad. The tissue is of sufficient additional width so as to allow the longitudinal peripheral portions of the tissue layer to overlap on the body facing surface of the pad, securely holding the wrapper with its body impervious laminate in position for cutting and other handling.

A similar solution has been proposed in U.S. Pat. No. 3,230,955 wherein a fluid impervious sheet laminated to a tissue is employed as above with the exception that the tissue and impervious sheet are co-extensive and are held about the product by virtue of a "bridging" tissue ply which overlies the entire body facing surface of the product.

While both these methods are effective for facilitating the processing of napkins with impervious layers, they suffer from a common drawback which is particularly significant in view of recent efforts to produce a relatively stain free cover. Specifically, the extended portion of the cover overlying the body facing side of the napkin as disclosed in Canadian Patent 805,351 or the bridging ply, also overlying the body facing side of the napkin, as disclosed in U.S. Pat. No. 3,230,955 are both constructed of highly wicking material, e.g., tissue, primarily because of cost considerations. As such, when these materials are wetted with body fluid, they tend to wick such fluid laterally across the entire body facing surface of the napkin. As a result, notwithstanding the use of the recently developed non-wicking covers, the layer immediately below such cover becomes stained over a wide area, and this wide stain is visible through the cover and may even allow fluid to strike back through the cover, thus frustrating the purpose of these new covers. In view of the above problems, a need has arisen for a napkin construction which can facilitate the placement and stability of the impervious layer during manufacture but which will not frustrate the desirable clean and dry appearance of the napkin after use.

SUMMARY OF THE INVENTION

In accordance with this invention a napkin construction has been discovered which obviates the stain propagating properties of the prior constructions and which still facilitates rapid placement and stability of the impervious layer during manufacture.

Specifically a wrapper is provided in a sanitary napkin which napkin comprises an elongated absorbent pad having a body facing surface and a garment facing surface with longitudinal sides therebetween. The wrapper is provided to overlie the garment facing surface, the longitudinal sides and the longitudinal, peripheral portions of the body facing surface of the pad. The wrapper comprises a body fluid impervious sheet laminated to a fibrous sheet, the fibrous sheet being wider than the impervious sheet so that the fibrous sheet extends beyond the fluid impervious sheet. In accordance with the teachings of this invention the impervious sheet has a width sufficient for the sheet to overlie the garment facing surface and at least a portion of the longitudinal sides of the pad. The fibrous sheet has a width sufficient to overlie the garment facing surface, the longitudinal sides and the longitudinal peripheral portions of the body facing surface of the pad; but such width is insufficient to overlie the central, major portion of the body facing surface of the pad.

In view of the above description, it can be seen that the wrapper of the sanitary napkin of this invention does not contribute any overlying wicking layer to the major central portion of the body facing surface of the pad. When used in conjunction with a relatively nonwicking cover, no wicking layer overlies this surface of the pad and only a small stain results. It should be noted in this connection, that while the primary object is to utilize the structure of this invention with a relatively nonwicking cover, even when used in conjunction with a wicking cover, the construction of this napkin will ameliorate the appearance of stain to a substantial degree.

Surprisingly, it has been discovered that, in contrast to the prior art teachings, there is no need to provide for overlapping of the fibrous layer or for a "bridging ply" in order to rapidly manufacture the product described herein. Unexpectedly, by having the fibrous layer extend onto only a small fraction of the body facing surface of the pad, i.e., at the longitudinal peripheral portions of such body facing surface, sufficient frictional engagement is generated to hold the laminate wrapper in place. Preferably, the frictional engagement is enhanced by employing the laminate wrapper in the product with the wrapper's fibrous face against the pad in all areas where they engage, i.e., at the garment facing side, the longitudinal sides and the longitudinal peripheral portions of the body facing side of the product.

BRIEF DESCRIPTION OF THE DRAWINGS

FIG. 7 is a perspective view of the wrapper employed in the napkin of FIG. 1.

DETAILED DESCRIPTION OF THE INVENTION

Figure 1:
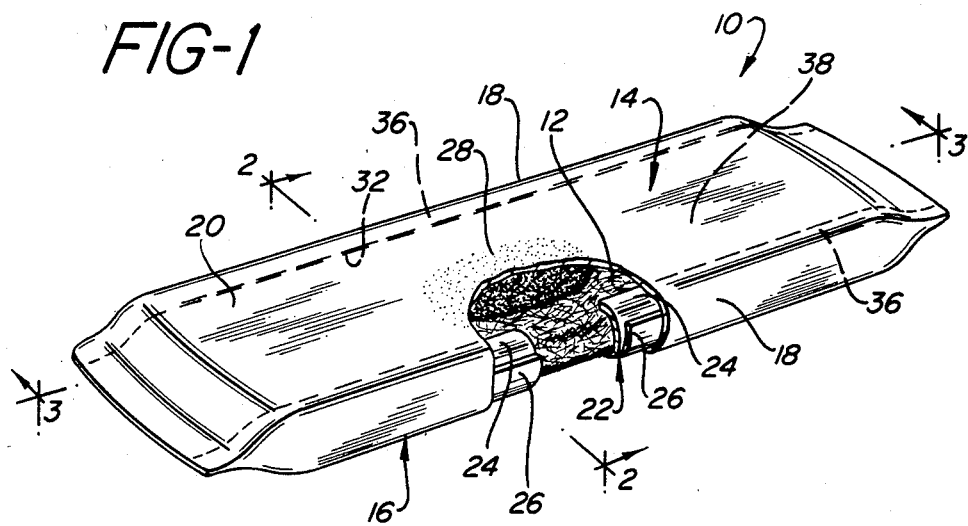
FIG. 1 is a perspective view of the sanitary napkin of this invention illustrated with parts removed to expose the internal construction.
Figure 2:
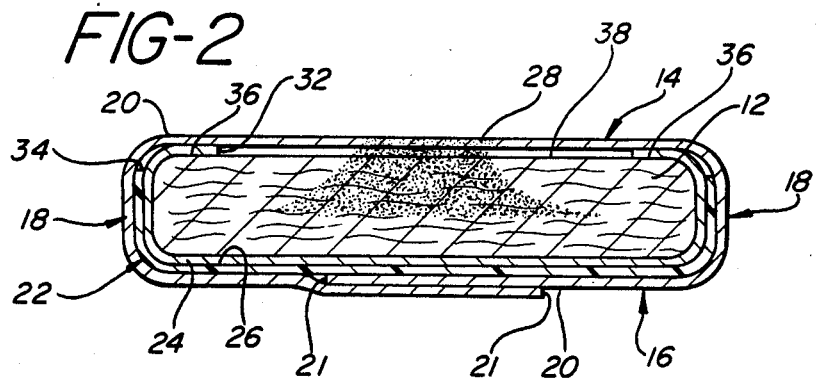
FIG. 2 is a transverse, cross-sectional view of the napkin of FIG. 1, taken through line 2—2.
Figure 3:
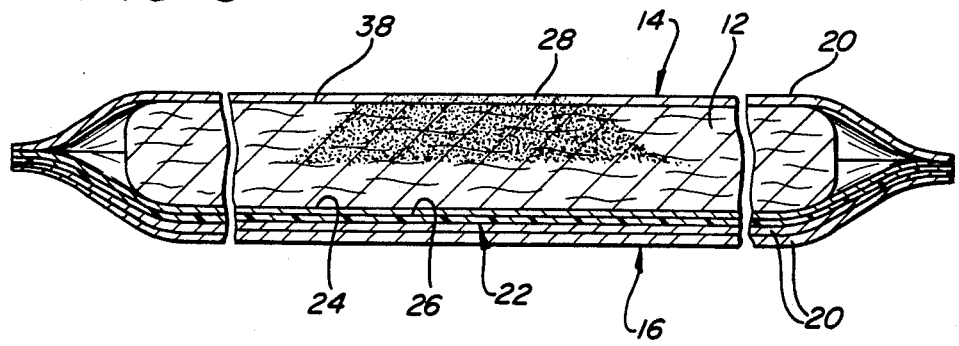
FIG. 3 is a longitudinal, cross-sectional view of the napkin of FIG. 1, taken through line 3—3.

Referring now to FIGS. 1-3 of the drawings, illustrated therein in perspective and cross-sectional views is a sanitary napkin 10 embodying the teachings of this invention. The napkin 10 comprises a generally planar pad 12 having two major surfaces; one of which is to be applied facing the body of the user, i.e., body facing surface 14, and the other which is to be applied facing the undergarment of the user, i.e., garment facing surface 16. Between these surfaces 14 and 16 are longitudinal sides 18.

The pad 12 may consist of loosely associated absorbent hydrophilic materials such as cellulose fibers, e.g., wood pulp, regenerated cellulose, or cotton fibers; other chemically or physically modified cellulosic fibers; other polymeric absorbent materials, both natural and synthetic, such as for example, hydrophilic foams (e.g., hydrophilic polyurethane foam). These materials may be used alone or in combination and may take various physical shapes and forms such as for example, layers of wadded tissue paper or molded foam structures or the like.

A menstrual fluid pervious cover 20 envelops the body facing surface 14, the longitudinal sides 18 and the garment facing surface 16 of pad 12. Generally, this cover is a single rectangular sheet of material having a width sufficient to encircle the pad 12 and having the longitudinal side edges 21 overlap and be sealed together on the garment facing surface of the napkin. The cover 20 may be any woven or nonwoven material pervious to body fluid striking its surface, such covers being well-known in the art and usually comprising cellulosic materials such as cotton or rayon. Recently, in an effort toward providing a nonstained clean and dry appearance, such covers have been comprised essentially of nonwettable, nonwicking hydrophobic material such as polyester or polyolefin fibers, e.g., polypropylene fibers. Additionally, films of materials such as polyethylene or polypropylene, have been employed, such films having apertures therethrough to render them permeable to menstrual fluid.

Sandwiched between the cover 20 and the pad 12 is, in accordance with the teachings herein, a wrapper 22 which, as best viewed in FIG. 7, comprises a laminate of a fibrous sheet 24 and a fluid impermeable sheet 26. The fluid impermeable sheet 26 is generally rectangular and is provided to preclude body fluid absorbed and retained by the pad 12 from reaching the external portions of the napkin in contact with the wearer's garment. Accordingly, the impermeable sheet 26 may comprise any thin, flexible menstrual fluid impervious material such as, for example, polymeric films, e.g., polyethylene, polypropylene or cellophane. Such film may be employed in thickness of about 0.1 to about 3.0 mils and preferably in thickness of about 0.2 to 1.0 mils.

The fibrous layer 24 may comprise any fibrous woven or nonwoven sheet material having sufficient strength and integrity to function in accordance with the teachings of this invention. For purposes of economy, tissue paper is employed which is both inexpensive and readily available in roll form and hence easily incorporated into the products of this invention. Preferably the tissue has a basis weight of 10 to about 30 gm/m$^2$ and still more preferably from about 13 to about 26 gm/m$^2$.

As best viewed in FIG. 7, the fibrous layer 24 is joined to the impervious layer 26 in face-to-face relationship to form the wrapper 22. This joining may be accomplished by use of adhesives, e.g., emulsion adhesives which set after drying or hot melt adhesives which are adhesively activated by heat at a specific temperature and then rapidly cool and set. Alternatively, the method described in Canadian Patent 805,351 (incorporated herein by reference) may be employed whereby the impervious sheet is of a thermosoftening synthetic plastic material e.g., polyethylene, and is bonded to the fibrous sheet by means of an intermediate thermosoftening plastic film having a softening point lower than that of the impervious sheet.

In accordance with the teachings of this invention, the width of the impermeable sheet 26 (dimension W$_2$ in FIG. 7) is sized to be sufficient for the sheet 26 to overlie the garment facing surface 16 of the pad 12 and at least a portion of the longitudinal sides 18 of pad 12. By "width of the impermeable sheet 26" it is meant the distance between longitudinally extending edges 34 which edges will lie gererally parallel to the longitudinal sides of the pad 12 when the wrapper 22 is in place about the pad 12.

Further, the width of the fibrous sheet 24 (dimension W$_1$ in FIG. 7) is sized to be sufficient for the sheet 26 to overlie the garment facing surface 16 of the pad 12, the longitudinal sides 18 of pad 12 and the longitudinal peripheral portions of the body facing surface of the pad 10. The width, $W_2$, is however, insufficient to have the fibrous sheet overlie the central major portion of the body facing surface of the pad 12. It will be understood that by "width of the fibrous sheet 24" it is meant the distance between longitudinally extending edges 32 which edges will lie generally parallel to the longitudinal sides of the pad 12 when the wrapper 22 is in place about pad 12.

Referring back to FIGS. 1–3, the wrapper is illustrated in place about the pad 12. As can be seen, by incorporating the teachings of this invention, the impervious sheet 26 overlies the garment facing surface 16 of the pad 12 and continues partially up the longitudinal sides 18 of the pad 12. The fibrous sheet 24 overlies the garment facing surface 16, the longitudinal sides 18 and the longitudinally extending, peripheral portions 36 of the body facing surface 14 of pad 12. The major central portion 38 of the body facing surface of pad 12 is free of the fibrous sheet. 24. By the term "major central portion" being free of sheet 24 it is meant that at least 30% of the body facing surface of pad 12 is free of the fibrous sheet. Preferably at least 40% of the body facing surface of pad 12 is so uncovered. For processing reasons it is preferable that no more than 85% of the major central position be exposed and preferably no more than 60%. Thus, for example, in a pad 12 2.375 inches wide, only 0.6 inches on either longitudinal side is covered with fibrous sheet 24. Preferably less than about 0.8 inch on either side are covered.

The value of leaving the major central portion 38 uncovered is clear from consideration of the stain pattern, shown schematically in FIGS. 1–3. The area 28 illustrates the stain on pad 12 and is limited to essentially the central portion of the outer surface of the napkin. There being no wicking medium intermediate the cover 20 and the pad 12, liquid striking the cover 20 at area 28 is drawn directly into the pad and away from the body facing surface 14. Hence only a small stain appears on the cover 20.

Figure 4:
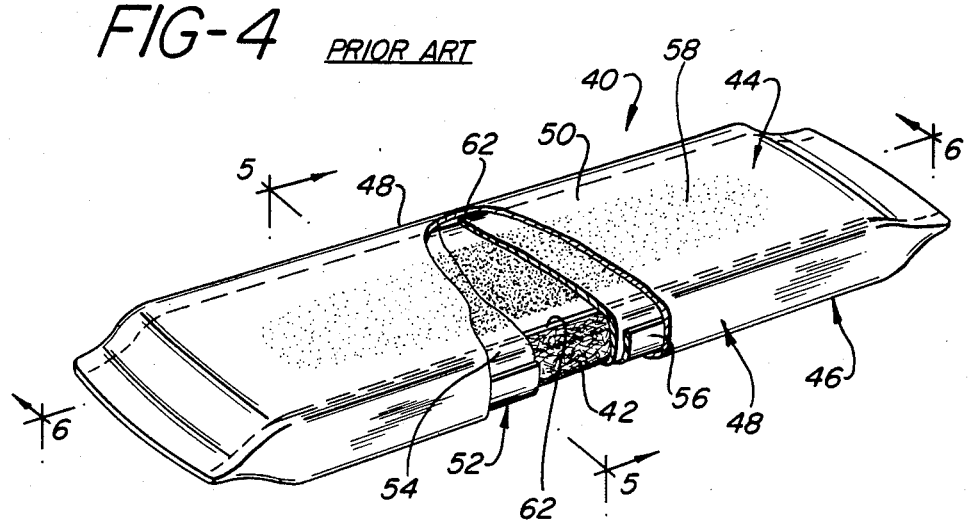
FIG. 4 is a perspective view of a prior art sanitary napkin illustrated with parts removed to expose the internal construction.
Figure 5:
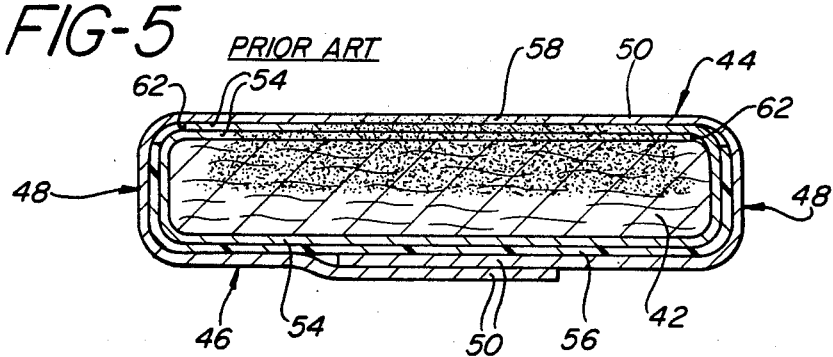
FIG. 5 is a transverse, cross-sectional view of the napkin illustrated in FIG. 4.
Figure 6:
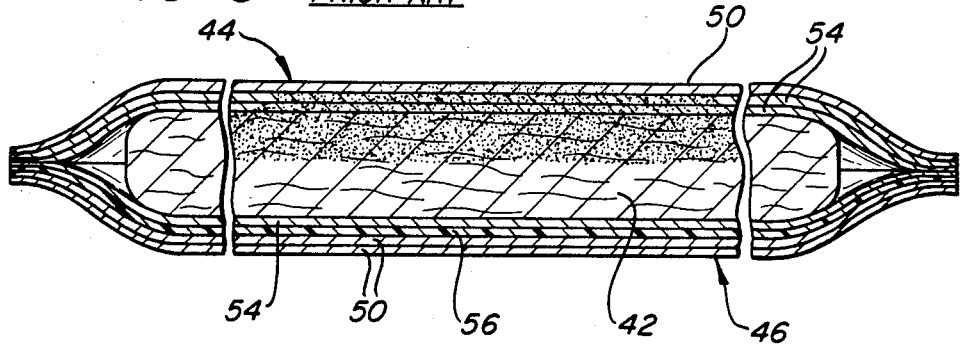
FIG. 6 is a longitudinal, cross-sectional view of the napkin illustrated in FIG. 4.

This situation should be contrasted to that which exists in the prior art napkin 40 illustrated in FIGS. 4–6. Napkin 40 is similar in most respects to that to napkin 10 of FIGS. 1–3. Accordingly, napkin 40 comprises a pad 42, having body facing surface 44, garment facing surface 46, and longitudinal sides 48. A menstrual fluid pervious cover 50 is provided to envelop the pad and overlap on the garment facing surface thereof.

Sandwiched between cover 50 and pad 42 is a wrapper 52 which also comprises a laminate of a fibrous sheet 54 and a fluid impermeable sheet 56. While the sheet 56 is essentially the same width as sheet 26 of napkin 10, it should be noted that in accordance with prior art practice, sheet 54 is of sufficient width to completely cover the body facing surface of the pad 42 and, in fact, is wide enough so that the longitudinal edges 62 of sheet 54 overlap on the body facing surface.

Accordingly, fluid deposited in a central area of the napkin will readily pass through the cover 50. At this point however, such fluid will encounter the highly wickable fibrous sheet 54. As a result, before fluid will be drawn into the absorbent pad 42 and away from body facing surface 44, fluid will be carried laterally across the body facing surface of the napkin by the wicking fibrous sheet 54. Such fluid spread will be apparent through the cover 50 as a wide stain area 58.

It can thus be seen that by following the teachings of this invention and providing the major central portion of the body facing surface of pad 12 uncovered by the fibrous sheet, a small stain pattern will result. Surprisingly, the failure to fully extend the fibrous sheet over the entire body facing surface does not have the concommitant result of making it more difficult to place and stabilize the wrapper during production. It has now been discovered that the frictional engagement between the fibrous sheet and the pad at the area of the longitudinal peripheral portion of the body facing surface of the pad is sufficient to carry on high speed manufacturing without any difficulty in placing or maintaining the wrapper in its proper position. This is particularly so when the frictional engagement is enhanced by placing the wrapper about the pad with the fibrous sheet portion in contact with the pad surfaces.

To illustrate the advantages of the teachings of this invention, the following example is given:

EXAMPLE

A series of napkins are prepared having the construction of that shown in FIGS. 1 through 3. A second series of napkins are prepared having the structure of the prior art napkins illustrated in FIGS. 4 through 6. The napkins of both series each have an overall length of 9.72 inches, a napkin width of 3.75 inches, and a thickness of 0.69 inches. The pads have an overall length of 7.68 inches and comprise woodpulp. Each napkin is enveloped by an outer cover having a width of 7.125 inches and overlapped on the garment facing side of the napkin. The cover comprises a nonwoven fabric of polyester fibers. The series of napkins following the prior art construction have, sandwiched between the pad and the cover, a laminate of polyethylene and absorbent tissue. The width of the tissue measures 7 inches and is overlapped across the body facing side of the napkins. The series of napkins embodying the teachings of this invention have a similar laminate of polyethylene and tissue sandwiched between the cover and the pad; however, the width of the tissue measures 4 ½ inches and, hence, extends only onto the peripheral portions of the body facing surface of the pad.

Each of the napkins are tested to determine visible stain area. In accordance with this test, each napkin is placed on a flat, clean level surface. A plexi-glass plate measuring 10 inches by 5 inches by 0.5 inches thick and containing a centrally located eliptical orifice having a major diameter of 1.5 inches and a minor diameter of 0.75 inches is placed on a napkin with the longitudinal direction of the orifice aligned with a longitudinal direction of the pad and with the orifice centered on the pad. A graduated cylinder is filled with various volumes of an ersatz menstrual fluid which fluid is selected to be a mixture having the ionic concentration, viscosity, and surface tension similar to menstrual fluid. The fluid also contains a coloring agent to simulate menstrual fluid. The ersatz menstrual fluid is then poured into the orifice maintaining the orifice filled without permitting its overflow until all the menstrual fluid has been absorbed into the napkin. The plate is then removed and the napkin is left to equilibrate for one minute. A 1 mil thick clear transparent plastic film measuring 10 inches by 5 inches is placed on the napkin and the outline of the visible stain is traced onto the film using a felt tip marker. The area of the tracing is then measured with a planimeter manufactured by the Keuffel & Esser Company and sold by them as a "Compensating Polar Planimeter". The result of this test is given in Table I below wherein the column designated "Full Tisue" is the measured stain area for the prior art series of napkins and the column designated "Partial Tissue" is the measured stain area for the series of napkins incorporating the teachings of this invention.

TABLE I

| Fluid Quantity | Stain Area (in$^2$) | |
|---|---|---|
|  | Full Tissue | Partial Tissue |
| 15 ml | 2.55 | 1.63 |
| 10 ml | 2.67 | 1.23 |
| 5 ml | 2.13 | 0.78 |

As can be seen from Table I, in each case of the various volumes of fluid applied the prior art, full tissue, napkins exhibited a far greater stain area than those of the partial tissue napkins of this invention.

What is claimed is:

1. A sanitary napkin comprising: an elongated absorbent pad having a body facing surface and a garment facing surface with longitudinal sides therebetween;
    a wrapper overlying said garment facing surface, said longitudinal peripheral portions of said body facing side;
    said wrapper comprising a body fluid impervious sheet laminated to a fibrous sheet, said fibrous sheet being wider than said impervious sheet so that said fibrous sheet extends beyond the fluid impervious sheet;
    said impervious sheet having a width sufficient for said impervious sheet to overlie the garment facing surface and at least a portion of said longitudinal sides of said pad;
    said fibrous sheet having a width sufficient to overlie the garment facing surface, the longitudinal sides, and the longitudinal peripheral portions of the boby facing side of the pad and extend beyond the edges of the impervious sheet but insufficient to overlie the central, major portion of said body facing side of said pad;
    said wrapper being emplaced about said pad with the fibrous sheet portion in contact with the garment facing surface, the longitudinal sides, and the longitudinal peripheral portions of the body facing side of the pad.

2. The sanitary napkin of claim 1 further provided with a cover enveloping said pad and said wrapper.

3. The sanitary napkin of claim 2 wherein said cover comprises hydrophobic material pervious to body fluids.

4. The sanitary napkin of claim 1 wherein said central major portion of said body facing side of said pad which is uncovered by said fibrous sheet comprises at least 30 percent of the total area at said body facing side of said pad.

5. The sanitary napkin of claim 4 wherein the central major portion of said body facing side of said pad uncovered by said fibrous sheet comprises at least 40 percent of the total area of said body facing side of said pad.

6. The sanitary napkin of claim 1 wherein the central major portion of said body facing side of said pad uncovered by said fibrous sheet comprises no more than 85 percent of the total area of said body facing side of said pad.

7. The napkin of claim 1 wherein the central major portion of said body facing side of said pad uncovered by said fibrous sheet comprises no more than 60 percent of the area of said body facing side of said pad.

8. The sanitary napkin of claim 1 wherein said fibrous sheet is tissue.

9. The sanitary napkin of claim 8 wherein said tissue has a basis weight of from about 10 to about 30 grams/meter$^2$.

10. The sanitary napkin of claim 9 wherein the tissue has a basis weight of from about 13 to about 26 grams/meter$^2$.

11. The sanitary napkin of claim 1 wherein said impervious sheet is a film of polyethylene.

12. The sanitary napkin of claim 11 wherein said polyethylene has a thickness of 0.1 to about 3.0 mils.

13. The sanitary napkin of claim 12 wherein said polyethylene film has a thickness of about 0.2 to about 1.0 mils.

* * * * *

UNITED STATES PATENT AND TRADEMARK OFFICE
CERTIFICATE OF CORRECTION

PATENT NO. : 4,675,013
DATED : June 23, 1987
INVENTOR(S) : Angelo P. Ruffo

It is certified that error appears in the above—identified patent and that said Letters Patent is hereby corrected as shown below:

Claim 1, column 7, line 24: "longitudinal peripheral" should read -- longitudinal sides and longitudinal peripheral--.

Signed and Sealed this

Nineteenth Day of July, 1988

Attest:

DONALD J. QUIGG

Attesting Officer          Commissioner of Patents and Trademarks